United States Patent [19]

Sessions et al.

[11] Patent Number: 5,065,752

[45] Date of Patent: Nov. 19, 1991

[54] HYDROPHILIC FOAM COMPOSITIONS

[75] Inventors: Robert W. Sessions, Hindsdale; Roy D. Carr, Burr Ridge, both of Ill.

[73] Assignee: Ferris Mfg. Co., Burr Ridge, Ill.

[21] Appl. No.: 705,938

[22] Filed: May 28, 1991

Related U.S. Application Data

[62] Division of Ser. No. 175,036, Mar. 29, 1988.

[51] Int. Cl.$^5$ .................... A61L 15/00; A61L 15/16
[52] U.S. Cl. .................... 128/156; 428/317.1; 428/304.4
[58] Field of Search ............. 128/156; 428/304.4, 428/317.1

[56] References Cited

U.S. PATENT DOCUMENTS

| | | | |
|---|---|---|---|
| Re. 32,476 | 8/1987 | Kistner | 405/268 |
| 2,017,596 | 10/1935 | Hoffman | 424/447 |
| 2,900,278 | 8/1959 | Powers et al. | 521/55 |
| 2,957,834 | 10/1960 | Moller et al. | 523/132 |
| 2,983,394 | 5/1961 | Novak | 47/48.5 |
| 3,419,006 | 12/1968 | King | 604/290 |
| 3,419,506 | 12/1968 | Gander | 523/111 X |
| 3,586,648 | 6/1971 | Sambeth et al. | 521/109.1 |
| 3,798,836 | 3/1974 | Rubens et al. | 47/63 |
| 3,805,532 | 4/1974 | Kistner | 405/264 |
| 3,889,417 | 6/1975 | Wood et al. | 47/58 |
| 3,961,629 | 6/1976 | Richter et al. | 604/369 |
| 3,973,355 | 8/1976 | McKenzie | 47/59 |
| 4,055,184 | 10/1977 | Karami | 604/359 |
| 4,069,177 | 1/1978 | Smith | 523/111 X |
| 4,132,839 | 1/1979 | Marans | 523/111 X |
| 4,137,200 | 1/1979 | Wood et al. | 521/159 |
| 4,156,067 | 5/1979 | Gould | 424/445 X |
| 4,181,637 | 1/1980 | Busch et al. | 524/710 |
| 4,188,447 | 2/1980 | Ehlenz | 428/290 |
| 4,190,563 | 2/1980 | Bosley et al. | 523/111 |
| 4,194,998 | 3/1980 | Fanta et al. | 527/314 |
| 4,241,537 | 12/1980 | Wood | 47/77 |
| 4,306,551 | 12/1981 | Hymes et al. | 128/156 |
| 4,307,717 | 12/1981 | Hymes et al. | 128/156 |
| 4,339,550 | 7/1982 | Palinczar et al. | 521/99 |
| 4,341,215 | 7/1982 | Eldridge | 604/368 |
| 4,363,319 | 12/1982 | Altshuler | 128/156 |
| 4,374,208 | 2/1983 | Fallows et al. | 521/109.1 |
| 4,394,930 | 7/1983 | Korpman | 220/444 |
| 4,410,571 | 10/1983 | Korpman | 427/385.5 |
| 4,411,262 | 10/1983 | von Bonin et al. | 523/111 |
| 4,412,036 | 10/1983 | Pedersen et al. | 525/54.26 |
| 4,415,388 | 11/1983 | Korpman | 156/78 |
| 4,497,914 | 2/1985 | Allen, Jr. et al. | 523/105 |
| 4,517,326 | 5/1985 | Cordts et al. | 524/310 |
| 4,554,317 | 11/1985 | Behar et al. | 525/28 |
| 4,579,578 | 4/1986 | Cooke | 71/11 |
| 4,614,787 | 9/1986 | Szycher et al. | 528/75 |
| 4,617,326 | 10/1986 | Bjornberg et al. | 428/536 |
| 4,625,720 | 12/1986 | Lock | 128/156 |
| 4,631,227 | 12/1986 | Nakamura | 428/283 |
| 4,664,662 | 5/1987 | Webster | 604/369 |
| 4,668,564 | 5/1987 | Orchard | 428/246 |
| 4,671,267 | 6/1987 | Stout | 128/156 |
| 4,675,009 | 6/1987 | Hymes et al. | 604/304 |
| 4,693,713 | 9/1987 | Chmelir et al. | 604/368 |

FOREIGN PATENT DOCUMENTS 0184233  6/1986  European Pat. Off. ............ 424/445

OTHER PUBLICATIONS

Hypol ® Laboratory Procedures and Foam Formulations, Published by W. R. Grace & Co.

Hypol Plus TM, Laboratory Procedures and Foam Formulations, Published by W. R. Grace & Co.

Witkowski and Parish, Cutaneous Ulcer Therapy, International Journal of Dermatology, vol. 25, No. 7, pp. 420-426, Sep., 1986.

*Primary Examiner*—Morton Foelak
*Attorney, Agent, or Firm*—Leydig, Voit & Mayer

[57] ABSTRACT

A hydrophilic foam composition comprising the in situ reaction product of an isocyanate-capped polyether prepolymer, a hydrophilic agent capable of absorbing water, an adjuvant comprising an alcohol, a wetting agent, and water.

10 Claims, No Drawings

HYDROPHILIC FOAM COMPOSITIONS

This is a divisional of copending application Ser. No. 175,036, filed on Mar. 29, 1988.

BACKGROUND OF THE INVENTION

1. Field of the Invention

The present invention relates to novel foam products and, more particularly, to highly absorbent hydrophilic polyurethane foam compositions which have liquid release and exchange characteristics.

2. Background of the Invention

Absorbent pads, such as for use in contact with the skin for absorbing body fluids, are well known. Such pads are useful for numerous applications, including for example as a diaper, sanitary napkin, bandage, wound dressing or the like.

Absorbent pads have been made of a wide variety of materials. For example, such pads have been made using graft copolymers, as described in U.S. Pat. No. 4,055,184. The absorbent pad therein described includes an absorbent mass comprising a solid finely-divided mixture of a completely hydrolyzed starch-polyacrylonitrile graft copolymer and a non-irritating and non-toxic water-soluble basic material such as, for example, sodium bicarbonate which may be admixed with and distributed in a highly porous web or batt of cotton linters, layers of creped tissue or a mass of shredded polyurethane foam particles.

Pads in the form of a foam and which have been made from various superabsorbent materials are likewise known. For example, U.S. Pat. No. 4,394,930 discloses an absorbent foam product prepared by mixing together a solid, particulate, water-insoluble, water-swellable polymer such as "hydrogels", "hydrocolloids" or "superabsorbents" which are lightly cross-linked polymers containing a plurality of hydrophilic groups, such as carboxyl, carboxamide, sulfonate salt or hydroxyl groups, a blowing agent, and a liquid polyhydroxy organic compound and allowing the mixture to foam.

Polyurethane foams, treated and/or prepared in a manner so as to render them hydrophilic are also known. For example, U.S. Pat. No. 3,586,648 discloses a hydrophilic polyurethane foam prepared by the so-called "one-shot" technique and is stated to include a carboxymethyl cellulose or a carboxymethyl cellulose salt.

U.S. Pat. No. 4,497,914 discloses an ostomy gasket composition derived from the non-aqueous reaction of a polyisocyanate and a polyoxyalkylene polyol. A hydrophilic filler, such as hydroxyethylcellulose, hydroxypropylcellulose or mixtures thereof, are incorporated into the polyol phase prior to reaction.

Hydrophilic cross-linked polyurethane foams are disclosed in U.S. Pat. No. 3,903,232. Such foams are prepared by reacting particular isocyanate-capped polyoxyethylene polyols having an isocyanate functionality greater than two with large amounts of an aqueous reactant, preferably water. The foam is said to be useful for the absorption of body fluids and may be used for external body cleaning, for internal body usage, such as is necessary in dental and medical applications, and as intimate absorptive products such as diapers, sanitary napkins, catamenial devices and the like.

Other adsorbent pads using hydrophilic foam include U.S. Pat. No. 3,961,629, which discloses a hydrophilic polyurethane foam in which the foam pores have a surfactant coating to accelerate absorption of body fluids into the pores at medically acceptable rates. The foam is rendered hydrophilic by coating the pore walls with a thin layer of a surfactant. Hygroscopic agents such as glycerine as well as other agents, such as germicidal and therapeutic agents, may be incorporated into the foam.

U.S. Pat. No. 4,664,662 discloses an absorbent wound dressing which comprises an absorbent foam material retained in a water permeable, porous bag. The absorbent foam is preferably a hydrophilic polyurethane foam which can be made from HYPOL isocyanate-capped polyether prepolymer marketed by W. R. Grace and Co. and non-ionic surfactants. Physiologically active components such as local anesthetics, antibacterial agents, antifungal agents and the like which are compatible with the absorbent material may be incorporated into the wound dressing.

Hydrophilic polyurethane foam compositions are also disclosed in U.S. Pat. No. 4,339,550. The hydrophilic foam composition is prepared by the "in situ" reaction of an isocyanate-capped polyether prepolymer having a functionality of from about 2 to about 8, water, and a chemically compatible, essentially nonpolar, volatile organic compound. The foam is stated to be capable of achieving a sustained, controlled release of the volatile materials from the foam structure. Suitable "control release" ingredients for use in controlling the rate of release of the volatile ingredients include polyols, such as propylene glycol and glycerin, and materials classified as gums.

Despite the wide variety of known absorbent pads and polyurethane foam compositions there still remains a need for a highly absorbent hydrophilic polyurethane foam composition which releasably carries an adjuvant and which is capable of both absorbing an external liquid and releasing the adjuvant carried by the foam composition in the presence of the external liquid.

Accordingly, it is a principal object of the present invention to provide a polyurethane foam composition which is hydrophilic, highly absorbent and which releasably carries an adjuvant which is capable of being released from the foam in the presence of an external liquid which is preferentially absorbed by the foam composition. A more detailed object of the present invention is to provide a foam composition which is capable of releasing an adjuvant to a designated situs and which is capable of absorbing external liquids from that situs. A related object is to provide such a polyurethane foam composition which will tightly hold the external fluid once it is absorbed.

Another object of the invention is to provide a hydrophilic foam composition that can be prepared at ambient temperature.

It is a further object of the present invention to provide a wound dressing using a highly absorbent hydrophilic polyurethane foam composition. It is yet another object of the present invention to provide such a foam composition which includes a therapeutic, cosmetic or other like agent for release to and treatment of the situs of application. A still further object is to provide a foam composition which has hemostatic, bacteriostatic, emollifying, demulcifying and wound cleansing properties.

It is yet another object to provide a method of treating a wound by applying to the wound a wound dressing which includes a hydrophilic foam composition as described herein.

A further object of the present invention is to provide a composite for use in a wound dressing which includes a hydrophilic foam composition as described herein. Another object is to provide a method for making such a composite.

These and other objects and advantages of the present invention will be apparent from the following description of the invention.

SUMMARY OF THE INVENTION

The present invention is predicated on the discovery that a highly absorbent hydrophilic polyurethane foam composition which releasably carries an adjuvant and is capable of releasing at least a portion of the adjuvant while preferentially absorbing external liquid upon exposure of the foam composition to the external liquid, can be made by incorporating a hydrophilic agent and a releasably carried adjuvant in the foam composition. Incorporation of the adjuvant in the resulting foam is achieved by the in situ reaction of a hydrophilic isocyanate-capped polyether prepolymer, a hydrophilic agent, water, adjuvant and a wetting agent.

Thus, in one aspect, the present invention provides a hydrophilic polyurethane foam composition comprising the in situ reaction product of an isocyanate-capped polyether prepolymer, a hydrophilic agent capable of absorbing water, an adjuvant comprising a mono or polyhydric alcohol, a wetting agent for enhancing the wettability of the foam composition, and water. The hydrophilic foam is capable of exchanging an external fluid and tightly carrying the external fluid in preference to at least a portion of the adjuvant so that upon exposure of the hydrophilic foam composition to an external fluid, such as, for example, to the exudate of a wound, the composition will absorb the external fluid and tightly carry it in preference to at least a portion of the adjuvant so that at least a portion of the adjuvant is released from the foam.

In another aspect, the present invention provides a novel wound dressing which incorporates the novel hydrophilic polyurethane foam. In yet another aspect, the present invention provides a method of treating a wound which includes applying to the wound the novel hydrophilic foam composition disclosed herein or a wound dressing made therefrom. In still other aspects of the invention, composites which include the hydrophilic foam composition described herein and a method for making such composites are provided.

While the invention will be described in connection with the preferred embodiments, it will be understood that the invention is not intended to be so limited. On the contrary, it is intended to cover all alternatives, modifications and equivalents as may be included within the spirit and scope of the invention as defined by the appended claims. As an example, while the present invention will be described herein in relation to the use of the highly absorbent hydrophilic foam composition as a wound dressing, it should be appreciated that the foam composition of this invention is likewise useful in other applications where it is desired to releasably carry an adjuvant to a situs for subsequent application and to absorb an external liquid, such as water, from the situs of application. Such uses include, for example, cosmetic applications.

DETAILED DESCRIPTION OF THE PREFERRED EMBODIMENTS

In accordance with the present invention there is provided a highly absorbent hydrophilic polyurethane foam composition which includes a releasably carried adjuvant which is capable of being emitted from the composition in the presence of an external liquid. The foam composition of this invention is the in situ reaction product of a reactant composition comprising an isocyanate-capped polyether prepolymer, a hydrophilic agent, an adjuvant, water and a surfactant or wetting agent.

In keeping with the invention, the hydrophilic foam composition, when applied to a moisture laden surface will preferentially absorb moisture from that surface while releasing the adjuvant carried by the composition. The hydrophilic polyurethane foam composition of the present invention is particularly useful as the absorbent pad of an occlusive or semi-occlusive wound dressing, commonly applied to injuries such as abrasions, incisions, punctures, lacerations, ulcers, sores, burns and the like to aid in stopping bleeding and in protecting the wound from contamination.

When applied to a wound, the foam composition of the present invention will absorb and retain a high volume of aqueous fluid, i.e., wound exudate, and will release the adjuvant to the wound situs. By proper selection of the adjuvant and, optionally, additives, such as therapeutic agents, medicaments and the like incorporated into the foam and releasably carried with the adjuvant, a wound dressing which incorporates the foam composition of the present invention may be prepared which is advantageously capable of providing enhanced hemostatic and chemical debridement characteristics as well as transdermal, bacteriostatic, emollifying, demulcifying and wound cleansing characteristics.

Once affixed to the skin surface, the foam composition absorbs exudate moisture from the wound. In absorbing the exudate moisture, the foam swells to conform to the wound contour so as to become thermally insulative to the surface of application, while at the same time holding moisture against the surface in order to keep that surface moist. The foam composition will then assist in maintaining a warm, moist and sealed wound with appropriate pH to promote epidermal resurfacing and re-epithelization. A wound dressing which includes the foam composition of the present invention does not adhere to the wound and thus does not cause reinjury upon its removal from the wound. This is believed to be due to the liquid exchange and the maintenance of a moist environment about the wound.

The hydrophilic polyurethane foam compositions of the present invention are prepared using an isocyanate-capped polyether prepolymer. Generally, these prepolymers must be safe for use in the human body, and are preferably capable of foaming in an aqueous system in the absence of a catalyst. On the other hand, such prepolymers should not dissolve in the aqueous liquid. Additionally, it is highly desirable that these prepolymers cure to form a porous cellular foam matrix to enable both absorption of external fluids and carriage of the chosen adjuvant in the foam composition. The formation of a cellular foam matrix is preferred due to a large volume available not only for absorption but the containment of the chosen adjuvant. It is further desirable that the prepolymers are capable of curing in the presence of water, in the absence of catalyst, and at ambient temperature.

Isocyanate-capped polyether prepolymers such as those disclosed in U.S. Pat. Nos. 3,903,232 and 4,137,200 are suitable for use in the present invention. These prepolymers have a defined average isocyanate functionality greater than 2. These prepolymers may be capped with aromatic isocyanates, such as, for example, toluene diisocyanate or methylene diphenyl isocyanate, or with aliphatic isocyanates, such as isophorone diisocyanate. Isocyanate-capped polyether prepolymers which have been found suitable for use in the practice of the present invention include prepolymers sold under the trademark HYPOL. Examples include HYPOL FHP 2000, HYPOL FHP 2002, HYPOL FHP 3000, HYPOL FHP 4000, HYPOL FHP 5000, HYPOL X6100 and HYPOL hydrogel.

HYPOL 2000, HYPOL 2002 and HYPOL 3000 prepolymers are derived from toluene diisocyanate. FHP 2000 and FHP 2002 both have an equivalent weight (per NCO) of 625, an NCO content of 1.60 meq/g and a specific gravity of 1.19. The viscosity of FHP 2000 is 18,500 cps (Brookfield LVF, #4 Spindle, 12 rpm at 25° C.) and that of FHP 2002 is 20,000. FHP 3000 has an equivalent weight (per NCO) of 425, an NCO content of 2.35 meq/g, a specific gravity of 1.15 and a viscosity (measured as described above) of 10,500. HYPOL hydrogel is likewise derived from toluene diisocyanate. It has an NCO content of 0.5-0.9 meq/g and a viscosity of 10,000 to 12,000 cps at 25° C.

Another example of an isocyanate-capped prepolymer suitable for use in the present invention and derived from toluene diisocyanate is AQUAPOL prepolymer, commercially available from Freeman Chemical Corporation. AQUAPOL prepolymers have an NCO-value of 2.5 to 3.0 and are formed from the reaction of toluene diisocyanate and an organic polyether polyol containing at least 40 percent by weight ethylene oxide adducts as described at Col. 2, lines 3-22 of U.S. Pat. No. 4,517,326.

A further example of an isocyanate-capped prepolymer suitable for use in the present invention and which is derived from toluene diisocyanate is sold under the trademark TREPOL, and is commercially available from Twin Rivers Engineering. TREPOL prepolymers have an -NCO content of 1.4 milliequivalents per gram and a viscosity at 90° C. of 4,700 cps.

The HYPOL FHP 4000 and HYPOL FHP 5000 prepolymers are derived from methylene diisocyanate. FHP 4000 has an equivalent weight (per NCO) of 476, an NCO content of 2.10 meq/g, a Brookfield viscosity (LVF, #4 Spindle, 12 r.p.m. at 25° C.) of 20,000 and specific gravity of 1.17. FHP 5000 has an equivalent weight (per NCO) of 392, an NCO content of 2.55 meq/g, a Brookfield viscosity (measured as for FHP 4000) of 18,000 and a specific gravity of 1.17.

An example of an isocyanate-capped prepolymer suitable for use in the present invention and derived from isophorone diisocyanate is HYPOL X6100. It has an —NCO content of 1.8 meq/grams and a viscosity at 25° C. of 12,000 cps.

The amount of prepolymer in the reactant composition used to prepare the hydrophilic foam composition is not particularly critical, but depends on a number of factors, including the proportion of other components in the reactant composition as will be described in greater detail hereinafter. However, there should be sufficient prepolymer to form a polyurethane foam, to releasably contain the adjuvant and to adequately contain the hydrophilic agent. To that end, the ratio of prepolymer to hydrophilic agent should be such that the reactant composition does not degrade or break up into its separate constituents. Furthermore, while there should be sufficient prepolymer to provide integrity to the foam matrix, there should not be so much prepolymer that the resulting polyurethane composition becomes unworkable. In short, and particularly where the final composition is to be applied to the skin, the resulting foam composition is desirably relatively smooth and soft while exhibiting the desired absorbence characteristics so that it does not irritate or otherwise harm the skin.

The concentration of prepolymer further depends on its isocyanate functionality and the degree of crosslinking desired in the final foam composition. In general, the greater the isocyanate functionality, the greater the degree of cross-linking in the cured foam matrix. Typically, the reactant composition will comprise from about 20% to about 60% by weight prepolymer. Preferably the reactant composition will comprise from about 45% to about 50% by weight of the prepolymer. Advantageously, the prepolymers may be used alone or in combination.

The reactant composition further includes a hydrophilic agent which is incorporated into the foam composition to absorb external liquid, such as wound exudate, and to retain such liquid in the composition. When applied to a wound, the hydrophilic agent is believed to work in conjunction with the foam matrix to hold moisture at the surface of the wound. This allows healing agents exuded by the wound to be concentrated and held at the wound surface. At the same time, the hydrophilic agent incorporated into the composition is believed to absorb fluid from the wound to assist thickening of the blood, i.e., it serves as a hemostat. The absorption of exudate by the hydrophilic agent, and the subsequent swelling of the agent results in the removal of inflammatory exudates and particles that would otherwise hinder tissue repair or cause eschar formation. Necrotic debris and bacteria are likewise removed as autolysis, i.e. chemical debridement is stimulated.

The hydrophilic agent is preferably a highly absorbent polymer, commonly known as a superabsorbent polymer. One measure of polymer absorbency is its fluid uptake capability, well known by those skilled in the art. Hydrophilic agents suitable for use in the present invention include polymers that are capable of absorbing at least 50 times their weight of water, that is, such agents have a fluid uptake of at least 50 ml/g. Hydrophilic agents having an even higher fluid uptake, such as of at least about 100 ml/g and even higher, that is, at least about 150 ml/g are preferred. Suitable superabsorbent polymers include sodium and aluminum salts of starch grafted copolymers of acrylates and acrylamides and combinations thereof, as well as polyacrylate salts. Of course, other absorbent materials may be used in combination with such highly absorbent polymers, provided the fluid uptake of the overall combination used for the hydrophilic agent is greater than 50 ml/g. When such agents are employed, either alone or in combination, the resulting foam composition desirably has the ability to hold at least about 3 times its weight in liquid. In the preferred embodiment, the resulting foam composition will have the ability to tightly hold at least about 3 times its weight in fluid. As used herein "tightly hold" or "tightly bound" liquid means the relative amount of liquid retained by the sample after compression, as described in detail hereinafter.

Hydrophilic polymers which have been found suitable for use in the foam composition of this invention are commercially available from Grain Processing Corporation. These polymers include a starch-g-poly(2-propenamide-co-2-propenoic acid, mixed sodium and aluminum salt) sold under the trademark WATER LOCK A-222; a starch-graft copolymer of polyacrylic acid and polyacrylamide having the chemical name starch-g-poly(2-propenamide-co-2-propenoic acid, sodium salt), sold under the trademark WATER LOCK A-100; a starch g-poly(2-propenamide-co-2-propenoic acid, sodium salt), sold under the trademark WATER LOCK A-200. Superabsorbent polymers commercially available from Grain Processing Corporation under the trademark WATER LOCK D-212 and WATER LOCK D-242 are likewise suitable. These polymers have the chemical name starch-g-poly(2-propenamide-co-2-propenoic acid, mixed sodium and aluminum salt). The superabsorbent polymer commercially available under the trademark WATER LOCK G-400 is also suitable for use in the making of the hydrophilic foam composition of the present invention. This superabsorbent polymer may be chemically identified as a poly(2-propenamide-co-2-propenoic acid, sodium salt). Other super absorbent powders suitable for use in the present invention are sold by Grain Processing Corporation under the trademark WATER LOCK B, C, and H.

Another example of a suitable superabsorbent polymer is poly-2-propenoic acid, sodium salt, sold under the trademark AQUA KEEP J-500 supplied by Sanyo Corp. In addition, super absorbent polymers sold by Arakawa Chemical (USA) Inc. under the trademark ARASORB are suitable. The preferred hydrophilic polymers are WATER LOCK A-100, A-200, A-222 and AQUA KEEP J-500. The hydrophilic polymers may be used alone, or in combination to achieve the desired absorptivity characteristics in the foam composition.

The hydrophilic agent may comprise additives in addition to the superabsorbent polymers, provided, as discussed above, the additives do not reduce the fluid uptake of the hydrophilic agent to below about 50 ml water per gram of hydrophilic agent and the fluid uptake of the final foam composition is not less than about 3 times its weight. Examples of such additives include methylcellulose, guar gum, pectin, karaya gum, chitosan, agar, acacia powder, carrageenan, gelatin and combinations thereof.

The amount of hydrophilic agent used and the type of it, in terms of its fluid uptake, that may be satisfactorily used to make the foam composition is not critical, but is, instead, dependent on the intended application of the composition. Stated another way, the greater the quantity of external liquid to be absorbed, e.g., the greater the amount of wound exudate, the greater the amount of hydrophilic agent that should be employed. In the alternative, the greater the amount of wound exudate to be absorbed, the greater the fluid uptake of the hydrophilic agent used, should be. For example, for an ulcerated wound where there is a high volume of wound exudate, a hydrophilic agent with high uptake is desirable. In addition, it may well be determined that the amount of hydrophilic agent may need to be increased. On the other hand, where the foam is to be applied to a small cut or light burn it may be suitable to use less hydrophilic agent or to use a hydrophilic agent with a lower fluid uptake. Determination of the type and amount of hydrophilic agent used is well within the ability of one skilled in the art in light of the disclosure herein.

The amount of hydrophilic agent should not be so great as to undesirably reduce the strength of the foam composition or result in a loss of polymer from the foam, although some loss of hydrophilic agent may be tolerated without adversely affecting the ability of the foam to absorb external liquid. The amount of hydrophilic agent employed in the reactant composition will also depend on the absorbency of the material used. As previously indicated, it is preferable that a sufficient amount of hydrophilic agent be employed so that the resulting foam composition is capable of absorbing at least about 3 times its weight in external liquid. Typically this can be achieved by including from about 5 wt. % to about 20 wt. % hydrophilic agent in the reactant composition.

The reactant composition of this invention further includes an adjuvant; preferably, a water-soluble adjuvant. The adjuvant is releasably carried by the resulting foam composition for subsequent release to a chosen situs of application. Release of the adjuvant occurs in the presence of an external liquid, such as wound exudate, which is preferentially absorbed by the foam composition. Absorption of the external liquid causes at least a portion of the adjuvant to be released.

It will be appreciated by those skilled in the art that not all of the liquid adjuvant is necessarily released (or need it be) in the presence of the external fluid. However, a sufficient amount of adjuvant must be released in order to achieve the desired result. To that end, it will be appreciated that the efficacy of the adjuvant is realized upon its release from the foam composition to the situs of application. In the case of a wound dressing, the situs is the wound, burn or the like, itself. Release of the adjuvant thus provides beneficial treatment to the wound.

Prior to curing, the adjuvant serves as a plasticizer for the reactant composition. It extends the curing time of the composition thereby allowing it to be more thoroughly mixed and formed. Once cured, the foam composition is softened by the adjuvant, allowing the foam to be more pliable and more easily applied to the skin surface or other surface of choice. Additionally, the adjuvant may be somewhat hygroscopic lending further to the hydrophilic nature of the foam composition.

Adjuvants suitable for use in the foam composition of the present invention are mono, di and polyhydric alcohols. Preferably the adjuvants are water soluble so that they may be readily released from the composition upon contact of the foam composition with an external liquid. For wound dressing applications, it is also desirable that the adjuvant be capable of contacting skin without adverse side effects. To that end, it is also preferable that the adjuvant comprise a chemical compound that will have the ability to open the skin pores to achieve a demulcent effect to relieve pain and/or irritation and to achieve an emollient effect to soften the skin and prevent maceration. It is also preferred that the adjuvant be compatible with therapeutic or other agents which may be carried by the adjuvant for subsequent delivery to the situs of application. Suitable adjuvants include water soluble alcohols, including monols, diols and polyhydric alcohols. Examples of monols include ethyl alcohol and isopropyl alcohol. Exemplary of suitable diols are propylene glycol, polyethylene glycol and polypropylene glycol. Exemplary of suitable polyhydric alcohols are glycerin, 1,2,4-butanetriol, trimethylolpropane, pentaerythritol and sorbitol. In general, the molecular weight of the alcohols should be less than about 1000. Mixtures of alcohols can likewise be used.

Glycerin is the preferred adjuvant because it has the attributes of a medicament, cosmetic or therapeutic agent. When glycerin is used and the hydrophilic agent is starch-based, it is believed that glycerin coats the hydrophilic agent to form a starch glycerite. When fluid is absorbed by the foam, glycerin is released, thereby allowing the hydrophilic agent to swell as it absorbs fluid from the wound and causing the foam to conform to the wound contour.

Various additional medicaments, cosmetics and therapeutic agents may be carried with the adjuvant and released with it to the desired situs. This release thus allows the transmission of such therapeutic or other agents carried in the adjuvant to the area of application outside the foam composition, further assisting in the beneficial treatment of the wound.

Illustrative of therapeutic agents which may be incorporated into the foam composition are Collasol 2400, Crotein SPA, Cromoist HYA, Crotein CAA and hydrocortisone acetate. Illustrative of cosmetic agents which may be incorporated into the foam composition are European Collagen Complex, Capture Complex Liposomes, Sardo ® bath oil, a hand lotion sold under the trademark Jergens ®, Noxema ® skin cream, Oil of Olay ® BF, Keri ® lotion, Vaseline ® herbal and aloe lotion, Ben Gay ® ointment and Retin-A ® cream.

The amount of adjuvant included in the reactant composition should preferably be sufficient to impart softness and pliability to the foam composition and be capable of delivering a therapeutic agent or the like, if included, to the environment of application. However, the volume of adjuvant should not be so great as to weaken or gel the composition. Generally, it has been found that the amount of adjuvant in the reactant composition should be from about 5 wt. % to about 30 wt. % of the reactant composition.

A wetting agent is included in the reactant composition to provide more uniform wettability of the resulting foam. The wetting agent also aids in controlling the cell size of the foam and in the reticulation of the final foam. Wetting agents suitable for use include non-ionic surfactants. Examples of materials that may be used as the wetting agent, either alone or in admixture, include block copolymers of ethylene oxide and propylene oxide sold under the trademark PLURONIC by BASF Wyandotte corporation, ethoxylated sorbitan fatty acid esters, glycerol esters, polyglycerol esters, and silicone fluids. PLURONIC F-68 and L-62 are preferred. As is known, PLURONIC F-68 aids in wound cleansing without causing tissue damage. The use of PLURONIC F-68 is especially preferred because of its cleansing action, particularly because a portion of the surfactant may be released when the foam composition is exposed to the exudate of the wound. Generally, the amount of wetting agent should be from about 1% to about 10% by weight of the reactant composition, preferably from about 5% to about 7% by weight.

The wetting agent should not react with the foam composition or any component of the foam formulation to create difficulties during foam formation or to adversely affect the desired characteristics of the foam composition in use or while being stored.

It should be appreciated that the source of the water required for the foaming reaction is not critical. The water so required may be provided as a separate component of the reactant composition, or, for example, it may be provided by one of the other components of the reactant composition. By way of illustration, and not in limitation, the required water may be provided with an aqueous-based cosmetic which may be incorporated into the foam composition.

The type of water used is likewise not critical. However, for medical applications, purified water such as deionized or distilled water may be used. Saline solutions may also be used satisfactorily.

It will be appreciated that the relative proportion of prepolymer, adjuvant and hydrophilic agent included in the reactant composition can be varied over wide ranges in order to prepare a hydrophilic foam composition having the desired release and exchange characteristics previously described, while likewise providing a foam composition that is aesthetically satisfactory, insofar as its oilyness, touch, appearance and general feel. In general, for use as a wound dressing, it is preferable that the foam composition be soft and generally smooth to the touch so that it does not irritate the skin. These characteristics may be achieved by properly balancing the relative proportion of adjuvant, prepolymer hydrophilic agent wetting agent and water.

By way of illustration, it has been found that if excess glycerin is used in the reactant composition the resulting foam composition has an extended cure time with decreased ability to tightly hold external liquid and it may have an oily or spongy nonuniform surface. On the other hand, if insufficient glycerin is included in the reactant composition, the resulting foam composition has been found to be less uniform, has relatively poor flow and porosity characteristics, has relatively poor dimensional stability, and absorbs liquid at a slower rate.

Similarly, if the relative proportion of prepolymer to hydrophilic agent is too high or too low, the resulting product will not be satisfactory. The amount of hydrophilic agent must be sufficient to absorb the external liquid and to promote the release of the adjuvant. If the amount of hydrophilic agent is too low, there is insufficient absorption of external liquid. On the other hand, if the amount of hydrophilic agent is too high, then the viscosity of the reactant composition will be too high for appropriate mixing.

In general, in order for the foam composition to have the desired liquid release and exchange characteristics and to provide a foam composition that is soft to the touch and not oily, the weight ratio of prepolymer to hydrophilic agent will desirably be in the range of from about 20:1 to about 20:10 and the ratio of prepolymer to adjuvant will desirably be in the range of from about 20:2 to about 20:30.

It will likewise be appreciated that the wetting agent employed and the amount thereof used may effect the characteristics of the resulting foam composition. It is generally desired that the wetting agent be used in an amount such that the foam is substantially uniform and readily wettable.

To effect foaming and the preparation of the hydrophilic polyurethane foam composition of the present invention it is preferred to prepare and mix an organic phase and an aqueous phase. The organic phase comprises the isocyanate-capped prepolymer and optionally, but preferably, the hydrophilic agent. The aqueous phase comprises the adjuvant, wetting agent, optionally the hydrophilic agent if it is not included in the organic phase, and other desired additives, such as, for example, dyes or the like to color the resulting foam. If a medicament, cosmetic or therapeutic agent is included in the reactant composition it will preferably be included in the aqueous phase. To prepare the foam, the organic phase and aqueous phase are simply mixed at room temperature, the resulting mixture is then cast or extruded, and the foam will form.

To prepare the foam for subsequent use in a wound dressing or the like the following process is preferred. A suitable substrate, such as a plastic (e.g. in the form of a sheet, laminate or fibrous mat), paper, foil, or the like is provided and coated with a medically acceptable adhesive. Such adhesives are generally well known to those skilled in the art. Then the reactant composition as described herein is poured directly onto the adhesive where the foam is formed. The foam may then be covered by a cover sheet if desired. The resulting composite which comprises the substrate, adhesive, and foam may be die cut and later used itself, or it may be used as part of an occlusive or semi-occlusive wound dressing.

The following examples will aid in demonstrating the present invention.

In all of the examples which follow a hydrophilic polyurethane foam composition was formulated by separately preparing an aqueous phase and an organic phase then mixing both phases at room temperature, and casting the mixture onto a film substrate.

The aqueous phase was prepared by dissolving the alcohol, wetting agent and colorant in distilled water using a laboratory grade magnetic stirrer. It should be noted that some surfactants (especially the paste types) required heating to 150° F. before dissolution or even dispersion was possible. All other mixing was done at ambient temperature. When Pluronic F-68 was used, solution required about one hour of mixing at 1000 rpm on the stirrer to complete dissolution.

The organic phase was prepared by mixing the isocyanate-capped prepolymer and hydrophilic agent for about 5 to 10 seconds in a plastic vessel using an electric drill with a paint mixer blade.

To prepare the foam composition, the aqueous phase was poured into the organic phase contained in a suitable mixing vessel. The two phases were then mixed using a drill with the paint mixer for about 15 to about 50 seconds at about 1200 rpm of the drill. Mixing time may be varied for different formulations, but generally mixing time was about 25 seconds.

The resulting mixture was evenly poured as a bead down a paper substrate coated with a medical grade adhesive, and covered with the silicone treated side of a 5 mil polystyrene sheet. The paper substrate was about four inches wide and bordered by 0.025 inch plastic strips to contain the mixture during compression. The bead was compressed and spread using a 30 pound steel cylinder. The mixture was rolled at the rate of two inches per second first at 90 seconds after the two phases are combined and then after 120 seconds after combination. The foam was allowed to set for approximately seven minutes, then the cover sheet was removed.

The resulting foams varied in thickness from about 0.050 inch to about 0.10 inch and varied in density from about 10 to about 20 lbs/ft$^3$.

Definitions

As used in the Examples appearing below, the following designations, symbols, terms and abbreviations have the indicated meanings:

I. Prepolymers

Prepolymer A denotes an isocyanate-capped polyoxyethylene polyol polyurethane prepolymer derived from toluene diisocyanate having an equivalent weight (per-NCO group) of 625, an NCO content of 1.6 meq/gram, a functionality (—NCO/mole) of 2.3 and a viscosity at 25° C. of 20,000 cps. (HYPOL 2002)

Prepolymer B denotes an isocyanate-capped polyoxyethylene polyol polyurethane prepolymer derived from toluene diisocyanate having an NCO content of 0.5–0.9 meq/g. and a viscosity at 25° C. of 10,000 to 12,000 cps. (HYPOL HYDROGEL)

Prepolymer C denotes an isocyanate-capped polyoxyethylene polyol polyurethane prepolymer derived from isophorone diisocyanate having an NCO content of 1.8 meq/gram and a viscosity at 25° C. of 12,000 cps. (HYPOL X6100)

Prepolymer D denotes an isocyanate-capped polyoxyethylene polyol polyurethane prepolymer derived from toluene diisocyanate having an —NCO content of 1.4 meq/gram and a viscosity at 90° C. of 4,700 cps. (TREPOL)

Prepolymer E denotes an isocyanate-capped polyoxyethylene polyol polyurethane prepolymer derived from methylenediphenyl diisocyanate having an NCO content of 2.55 meq/g, an equivalent weight (per-NCO group) of 392 and a viscosity at 25° C. of 18,000 cps. (HYPOL FHP 5000)

Prepolymer F denotes an isocyanate-capped polyoxyethylene polyol polyurethane prepolymer derived from methylenediphenyl diisocyanate having an equivalent weight (per-NCO group) of 476, an —NCO content of 2.10 meq/g and a viscosity at 25° C. of 20,000 cps. (HYPOL FHP 4000)

Prepolymer G denotes a diisocyanate prepolymer derived from toluene diisocyanate sold under the trademark AQUAPOL 035-0019 by Freeman Chemical Corporation.

II. Hydrophilic agents

A denotes a starch-g-poly(2-propenamide-co-2-propenoic acid, mixed sodium and aluminum salt) sold under the trademark WATER LOCK superabsorbent polymer A-222.

B denotes a starch-g-poly(2-propenamide-co-2-propenoic acid, sodium salt) sold under the trademark WATER LOCK superabsorbent polymer A-200.

C denotes a starch-g-poly(2-propenamide-co-2-propenoic acid, sodium salt) sold under the trademark WATER LOCK superabsorbent polymer A-100.

D denotes a polymer consisting of 2-propenoic acid, sodium salt sold under the trademark WATER LOCK superabsorbent polymer J-500.

E denotes an absorbent polymer sold under the trademark ARASORB.

F denotes a polyacrylic acid, sodium salt sold under the trademark AQUA KEEP J-500.

III. Absorption and Extraction Test

Each of the foams of Examples 1–57 was tested to determine the release characteristics of the foam, especially the adjuvant, and to determine the ability of the foam to absorb external liquid. The foams were immersed in one or more of the following: water, a normal saline solution, a 0.03% HCl solution and/or a 0.05% NaOH solution. The pH of these solutions fall within the range of pH 2 to pH 12. Both the liquid held by the sample and the liquid tightly held by the sample were measured.

The liquid held by the sample is reported as retained liquid. Retained liquid is the unit weight of liquid per unit weight of foam. It is determined by the formula:

$$\text{Retained Liquid} = \frac{\text{(Wt. of Foam Sample Absorbed Liquid)} - \text{(Weight of Foam Sample)}}{\text{Weight of Foam Sample}}$$

Tightly held liquid is a measure of the relative amount of liquid retained by the sample after compression. It is determined by rolling an 8 pound roller over the sample ten times, and then, using the retained liquid formula to calculate the relative proportion of liquid that was not squeezed out of the composition.

To determine whether the adjuvant is efficiently released from the foam, the % extractables is measured in deionized water, normal saline, 0.03% HCl and/or 0.05% NaOH solutions. The percent extractable material is determined under static conditions at room temperature. In addition, the dehydrated extracted residues were visually examined for the adjuvant. In general, it was found that from about 90 to 95% of the adjuvant is released from the foam. In general, when deionized water was used, the pH of the extract was 7.0±1.0 pH units.

The absorption rate was determined for the foam compositions. The absorption rate is the time, in seconds, for 0.1 g of fluid to be absorbed by the foam composition. The fluid used was either deionized water, distilled water or normal saline. An absorption rate of less than 10 is satisfactory, and a rate of less than 5 is preferred.

The data for these studies is set forth in Tables immediately following the Examples.

Unless otherwise noted, for the compositions set forth in the Tables hereinafter all parts are in part by weight.

EXAMPLES 1-8

These Examples illustrate reactant compositions used to make hydrophilic foams of the present invention. Examples 1-8 illustrate variations in the amount of water and in the wetting agent used in the reactant composition. Example 8 illustrates the wide range of the ratio of prepolymer to hydrophilic agent and prepolymer to adjuvant that can be employed in making the foam composition of this invention. The reactant compositions are set forth in Table I below.

The retained liquid, tightly held liquid, extractable materials and absorption rate for the foam compositions of Examples 1 through 8 are set forth in Table II.

TABLE I

| REACTANT COMPOSITION | EXAMPLE No. | | | | | | | |
|---|---|---|---|---|---|---|---|---|
| | 1 | 2 | 3 | 4 | 5 | 6 | 7 | 8 |
| I. PREPOLYMER | | | | | | | | |
| Prepolymer A | 20.00 | 20.00 | 20.00 | 20.00 | 20.00 | 20.00 | 20.00 | 9.00 |
| II. HYDROPHILIC AGENT | | | | | | | | |
| A | 2.00 | 2.00 | 2.00 | 2.00 | 2.00 | 2.00 | 2.00 | 3.00 |
| III. WATER | 14.50 | 10.00 | 14.50 | 10.00 | 12.25 | 15.00 | 13.00 | 18.00 |
| IV. ADJUVANT SYSTEM | | | | | | | | |
| glycerin | 5.00 | 5.00 | 5.00 | 5.00 | 5.00 | 5.00 | 5.00 | 15.00 |
| V. WETTING AGENT | | | | | | | | |
| Pluronic F-68 | 2.50 | | | | 1.25 | | | |
| Pluronic L-62 | | 1.00 | | | 0.50 | | | 0.70 |
| Pluronic F-88 | | | 2.50 | | | | | |
| Pluronic L-92 | | | | 1.00 | | | | |
| TMAZ 85 sorbitan trioleate | | | | | 2.00 | | | |
| Mazol 80 MG-K | | | | | | | 2.00 | |
| VI. DYES/DEFOAMING AGENTS | | | | | | | | |
| FD & C Blue No. 1 Solution | 0.05 | 0.05 | | | 0.025 | | | |
| FD & C Red No. 3 & 40 Solution | | | | 0.025 | | | | |

TABLE II

| RETAINED LIQUID | EXAMPLE NO. | | | | | | | |
|---|---|---|---|---|---|---|---|---|
| | 1 | 2 | 3 | 4 | 5 | 6 | 7 | 8 |
| Water | 5.4 | 5.3 | 6.1 | 6.4 | 5.6 | 6.2 | 5.9 | 7.1 |
| Tightly Held Water | 3.3 | 2.9 | 2.8 | 3.3 | 3.0 | 3.4 | 3.0 | 4.9 |
| % Extractable Material | 22.0 | 19.0 | 21.0 | 20.0 | 20.0 | 16.0 | 18.0 | 46.0 |
| Saline | 3.9 | 3.6 | — | — | 3.6 | 4.4 | — | — |
| Tightly Held Saline | 1.3 | 1.4 | — | — | 1.4 | 1.4 | — | — |
| % Extractable Material | 22.5 | 19.6 | — | — | 19.0 | 16.0 | — | — |
| 0.03% HCl Solution | 4.0 | 3.6 | 3.8 | 4.0 | 3.3 | — | — | — |
| Tightly Held 0.03% HCl Solution | 0.92 | 0.97 | 0.89 | 0.87 | 0.95 | — | — | — |
| % Extractable Material | 22.7 | 18.6 | 23.0 | 22.0 | 20.0 | — | — | — |
| 0.05% NaOH | 5.2 | 4.9 | 5.1 | 5.8 | 4.7 | — | — | — |
| Tightly Held 0.05% NaOH | 2.6 | 2.4 | 2.3 | 2.8 | 2.4 | — | — | — |
| % Extractable Material | 21.2 | 18.2 | 22.0 | 19.2 | 19.0 | — | — | — |
| ABSORPTION RATE | 3.0 | 3.0 | 2.0 | 3.5 | 1.0 | 6.0 | 1.0 | 2.5 |

As can be seen by the data in Tables I and II, all of the foams were satisfactory according to the desired physical and chemical criteria. The foams of Examples 1 and 2 are preferred.

EXAMPLES 9–18

These Examples illustrate reactant compositions suitable for preparing hydrophilic foam compositions of the present invention wherein various adjuvants and combinations of adjuvants are used. The reactant compositions are set forth in Table III.

The retained liquid, tightly held liquid, extractable materials and absorption rate for the foam compositions of Examples 9 through 18 are set forth in Table IV.

The foams of Examples 9–12, 17 and 18 were acceptable. However, the foams of Examples 13 and 15 exhibited gross porosity, while the foams of Examples 14 and 16 had excessively high absorption rates, and were thus more hydrophobic.

EXAMPLES 19–26

These Examples illustrate reactant compositions suitable for preparing hydrophilic foam compositions of the present invention wherein various prepolymers and mixtures of prepolymers are used in the reactant composition. The reactant compositions are set forth in Table V.

The retained liquid, tightly held liquid, extractable materials and absorption rate for the foam compositions of Examples 19 through 26 are set forth in Table VI.

TABLE III

| REACTANT COMPOSITION | 9 | 10 | 11 | 12 | 13 | 14 | 15 | 16 | 17 | 18 |
|---|---|---|---|---|---|---|---|---|---|---|
| I. PREPOLYMER | | | | | | | | | | |
| Prepolymer A | 20.00 | 20.00 | 20.00 | 20.00 | 20.00 | 20.00 | 20.00 | 20.00 | 20.00 | 20. |
| II. HYDROPHILIC AGENT | | | | | | | | | | |
| A | 2.00 | 2.00 | 2.00 | 2.00 | 2.00 | 2.00 | 2.00 | 2.00 | 2.00 | 2.00 |
| III. WATER | 14.50 | 14.50 | 14.50 | 14.50 | 14.50 | 14.50 | 14.50 | 14.50 | 14.50 | 14. |
| IV. ADJUVANT SYSTEM | | | | | | | | | | |
| 1,2,4-butanetriol | 5.00 | | | | | | | | | |
| trimethylol propane | | 5.00 | | | | | | | | |
| glycerin | | | 4.00 | 2.50 | | | | 2.50 | 4.00 | 4.50 |
| polypropylene glycol | 500 | | 1.00 | | | 5.00 | | 2.50 | 1.00 | |
| propylene glycol | | | | 2.50 | 5.00 | | | | | |
| ethyl alcohol | | | | | | | 5.00 | | | |
| pentaerythritol | | | | | | | | | | 0.50 |
| V. WETTING AGENT | | | | | | | | | | |
| Pluronic F-68 | 2.50 | 2.50 | 2.50 | 2.50 | 2.50 | 2.50 | 2.50 | 2.50 | 2.50 | 2. |
| VI. OTHER | | | | | | | | | | |
| FD & C Blue No. 1 Solution | 0.05 | 0.05 | 0.05 | 0.05 | 0.05 | 0.05 | 0.05 | 0.05 | 0.05 | 0 |

TABLE IV

| RETAINED LIQUID | 9 | 10 | 11 | 12 | 13 | 14 | 15 | 16 | 17 | 18 |
|---|---|---|---|---|---|---|---|---|---|---|
| Water | 4.7 | 5.9 | 4.4 | 5.9 | 5.1 | 4.7 | 7.6 | 3.8 | 4.4 | 6.6 |
| Tightly Held Water | 2.8 | 3.6 | 2.8 | 2.9 | 3.0 | 4.3 | 4.8 | 3.3 | 2.8 | 2.8 |
| % Extractable Material | 23.0 | 19.0 | 22.2 | 17.0 | 17.5 | 19.0 | 11.1 | 15.0 | 22.2 | 2.8 |
| Saline | 3.4 | 3.4 | 3.4 | — | 3.7 | 2.9 | 3.9 | 3.0 | 3.4 | — |
| Tightly Held Saline | 1.3 | 1.5 | 1.5 | — | 1.5 | 2.4 | 2.2 | 1.9 | 1.5 | — |
| % Extractable Material | 22.0 | 18.0 | 19.6 | — | 17.4 | 16.5 | 7.2 | 14.0 | 19.6 | — |
| ABSORPTION RATE | 5.5 | 4.5 | 4.5 | 2.0 | 2.0 | >60 | 2.5 | >60 | 4.5 | 2.0 |

TABLE V

| REACTANT COMPOSITION | 19 | 20 | 21 | 22 | 23 | 24 | 25 | 26 |
|---|---|---|---|---|---|---|---|---|
| I. PREPOLYMER | | | | | | | | |
| Prepolymer A | | 15.00 | | | | | | |
| Prepolymer B | 20.00 | 5.00 | | | | 10.00 | | 10.00 |
| Prepolymer C | | | | | | 10.00 | | |
| Prepolymer D | | | | | | | 20.00 | 10.00 |
| Prepolymer E | | | | 20.00 | | | | |
| Prepolymer F | | | | | 20.00 | | | |
| Prepolymer G | | | 20.00 | | | | | |
| II. HYDROPHILIC AGENT | | | | | | | | |
| A | 2.00 | 2.00 | 2.00 | 2.00 | 2.00 | 2.00 | 2.00 | 2.50 |
| D | | | | | | 2.00 | | 0.50 |
| III. WATER | | | | | | | | |
| Normal saline, 0.85% NaCl | 14.50 | 14.50 | 14.50 | 10.00 | 14.50 | 14.50 | 14.50 | 14.50 |
| IV. ADJUVANT SYSTEM | | | | | | | | |
| glycerin | 5.00 | 5.00 | 5.00 | 5.00 | 5.00 | 10.00 | 5.00 | 10.00 |
| honey | | | | | | 0.50 | | 0.50 |
| V. WETTING AGENT | | | | | | | | |
| Pluronic F-68 | 2.50 | 2.50 | 2.50 | | 2.50 | 2.50 | 2.50 | 2.50 |

TABLE V-continued

| REACTANT COMPOSITION | EXAMPLE No. | | | | | | | |
|---|---|---|---|---|---|---|---|---|
| | 19 | 20 | 21 | 22 | 23 | 24 | 25 | 26 |
| Pluronic L-92 | | | | 1.00 | | | | |
| VI. OTHER | | | | | | | | |
| FD & C Blue No. 1 Solution | 0.05 | 0.05 | 0.05 | | 0.05 | 0.05 | 0.05 | 0.05 |

TABLE VI

| RETAINED LIQUID | EXAMPLE NO. | | | | | | | |
|---|---|---|---|---|---|---|---|---|
| | 19 | 20 | 21 | 22 | 23 | 24 | 25 | 26 |
| Water | 7.1 | 5.4 | 5.9 | 3.1 | 3.8 | 8.5 | 7.9 | 10.0 |
| Tightly Held Water | 5.9 | 4.9 | 2.9 | 2.5 | 2.2 | 6.0 | 4.8 | 6.6 |
| % Extractable Material | 20.2 | 16.0 | 21.2 | 18.0 | 21.0 | 30.0 | 21.0 | 24.2 |
| Saline | 5.8 | 4.0 | — | — | — | — | — | — |
| Tightly Held Saline | 4.5 | 3.6 | — | — | — | — | — | — |
| % Extractable Material | 16.2 | 12.4 | — | — | — | — | — | — |
| ABSORPTION RATE | 4.0 | >60 | 3.0 | 1.0 | 1.0 | 75 | 2.5 | 2.5 |

The foams of Examples 21 and 26 were acceptable as determined by all visual and measured properties. However, the foams of Examples 19 and 20 exhibit relatively poorer dimensional stability and a slower absorption rate. The foams of Examples 22-25 were less uniform than the preferred composition of Examples 1 and 2.

EXAMPLES 27-32

These Examples illustrate the wide variety of hydrophilic agents that may be suitably employed in the reactant composition used to prepare the hydrophilic foam compositions of the present invention. The reactant compositions are set forth in Table VII.

The retained liquid, tightly held liquid, extractable materials and absorption rate for the foam compositions of these Examples are set forth in Table VIII.

TABLE VII

| REACTANT COMPOSITION | EXAMPLE No. | | | | | |
|---|---|---|---|---|---|---|
| | 27 | 28 | 29 | 30 | 31 | 32 |
| I. PREPOLYMER | | | | | | |
| Prepolymer A | 20.00 | 20.00 | 20.00 | 20.00 | 20.00 | 20.00 |
| II. HYDROPHILIC AGENT | | | | | | |
| D | 2.00 | | | | | |
| C | | | | 4.00 | | |
| E | | 2.00 | | | | |
| Carrageenan | | | 2.00 | | | |
| A | | | | | 2.00 | 2.00 |
| poly D-glucosamine | | | | | 1.00 | |
| pectin | | | | | | 2.00 |
| III. WATER | 14.50 | 14.50 | 10.00 | 10.00 | 14.50 | 10.00 |
| IV. ADJUVANT SYSTEM | | | | | | |
| glycerin | 5.00 | 5.00 | 5.00 | 5.00 | 5.00 | 5.00 |
| V. WETTING AGENT | | | | | | |
| Pluronic F-68 | 2.50 | 2.50 | 1.10 | | 2.50 | 2.50 |
| Pluronic L-62 | | | 1.00 | | | |
| VI. OTHER | | | | | | |
| FD & C Blue No. 1 Solution | 0.05 | 0.05 | | | 0.05 | |
| FD & C Red No. 3 & 40 Solution | | | 0.05 | 0.05 | | 0.05 |
| 10% Dimethyl-polysiloxane | | | | 0.10 | | |

TABLE VIII

| RETAINED LIQUID | EXAMPLE NO. | | | | | |
|---|---|---|---|---|---|---|
| | 27 | 28 | 29 | 30 | 31 | 32 |
| Water | 8.2 | 9.4 | 4.7 | 8.8 | 5.3 | 7.5 |
| Tightly Held Water | 6.6 | 6.0 | 0.92 | 4.5 | 2.8 | 2.5 |
| % Extractable Material | 20.7 | 20.7 | — | — | 22.0 | — |
| Saline | — | — | — | — | 3.9 | — |
| Tightly Held Saline | — | — | — | — | 1.3 | — |
| % Extractable Material | — | — | — | — | 21.0 | — |
| ABSORPTION RATE | 2.0 | 1.0 | 2.0 | 3.5 | 2.0 | 4.5 |

The foams of Examples 27-32 were all acceptable by all criteria. However, the tightly held liquid of Example 29 is somewhat low.

EXAMPLES 33-37

These Examples illustrate the addition of therapeutic agents suitable for use in wound dressing applications to the adjuvant of the reactant composition used to prepare hydrophilic foam compositions of the present invention. The reactant compositions are set forth in Table IX.

The retained liquid, tightly held liquid, extractable materials and absorption rate for the foam compositions of these Examples are set forth in Table X.

TABLE IX

| REACTANT COMPOSITION | EXAMPLE No. | | | | |
|---|---|---|---|---|---|
| | 33 | 34 | 35 | 36 | 37 |
| I. PREPOLYMER | | | | | |
| Prepolymer A | 20.00 | 20.00 | 20.00 | 20.00 | 20.00 |
| II. HYDROPHILIC AGENT | | | | | |
| A | 2.00 | 2.00 | 2.00 | 2.00 | 2.00 |
| III. WATER | 14.50 | 14.50 | 14.50 | 14.50 | 14.50 |
| IV. ADJUVANT SYSTEM | | | | | |
| glycerin | 5.00 | 5.00 | 5.00 | 5.00 | 5.00 |
| Collasol 2400 | 2.00 | | | | |
| Crotein SPA | | 2.00 | | | |
| Cromoist HYA | | | 2.00 | | |
| Crotein CAA | | | | 2.00 | |
| Hydrocortisone acetate, 0.5% | | | | | 2.00 |
| V. WETTING AGENT | | | | | |
| Pluronic F-68 | 2.50 | 2.50 | 2.50 | 2.50 | 2.50 |
| VI. OTHER | | | | | |
| FD & C Blue No. 1 Solution | 0.05 | 0.05 | 0.05 | 0.05 | 0.05 |

TABLE X

| RETAINED LIQUID | EXAMPLE NO. | | | | |
|---|---|---|---|---|---|
| | 33 | 34 | 35 | 36 | 37 |
| Water | 5.6 | 6.8 | 6.4 | 5.7 | 6.6 |
| Tightly Held Water | 2.6 | 2.7 | 2.8 | 2.3 | 2.7 |
| % Extractable Material | 23.0 | 24.0 | 20.0 | 29.0 | 21.0 |
| ABSORPTION RATE | 2.0 | 2.0 | 3.0 | 2.0 | 4.0 |

As can be seen by the data, all the foams of Examples 33-37 were acceptable.

EXAMPLES 38-47

These Examples illustrate the addition of cosmetic agents suitable for use in the hydrophilic foam compositions of the present invention. The reactant compositions are set forth in Table XI.

In Examples 43-47 the water needed for the foaming reaction was provided by the water contained by the cosmetic. The surfactant was also included in the cosmetic.

The retained liquid, tightly held liquid, extractable materials and absorption rate for the foam compositions of these Examples are set forth in Table XII.

TABLE XI

| REACTANT COMPOSITION | EXAMPLE No. | | | | | | | | | |
|---|---|---|---|---|---|---|---|---|---|---|
| | 38 | 39 | 40 | 41 | 42 | 43 | 44 | 45 | 46 | 47 |
| I. PREPOLYMER | | | | | | | | | | |
| Prepolymer A | 20.00 | 20.00 | 20.00 | 20.00 | 20.00 | 20.00 | 20.00 | 20.00 | 20.00 | 10. |
| II. HYDROPHILIC AGENT | | | | | | | | | | |
| A | 2.00 | 2.00 | 2.00 | 2.00 | 2.00 | 2.00 | 2.00 | 2.00 | 2.00 | 2.00 |
| III. WATER | 14.50 | 14.50 | 14.50 | 14.50 | 14.50 | — | — | — | — | — |
| IV. ADJUVANT SYSTEM | | | | | | | | | | |
| glycerin | 2.50 | 4.00 | 5.00 | 5.00 | 5.00 | 5.00 | 5.00 | 5.00 | 5.00 | 2. |
| European Collagen Complex | 2.50 | | | | | | | | | |
| Capture Complex Liposomes | | 1.00 | | | | | | | | |
| Sardo bath oil | | | 2.00 | | | | | | | |
| Jergens lotion | | | | 2.00 | | | | | | |
| Noxema skin cream | | | | | 2.00 | | | | | |
| Oil of Olay BF | | | | | | 20.00 | | | | |
| Keri lotion | | | | | | | 20.00 | | | |
| Vaseline Herbal & Aloe lotion | | | | | | | | 20.00 | | |
| Ben Gay ointment | | | | | | | | | 20.00 | |
| Retin-A cream | | | | | | | | | | 10.0 |
| V. WETTING AGENT | | | | | | | | | | |
| Pluronic F-68 | 2.50 | 2.50 | 2.50 | 2.50 | 2.50 | — | — | — | — | — |
| VI. OTHER | | | | | | | | | | |
| FD & C Blue No. 1 Solution | 0.05 | 0.05 | 0.05 | 0.05 | 0.05 | — | — | — | — | — |

TABLE XII

| RETAINED LIQUID | EXAMPLE NO. | | | | | | | | | |
|---|---|---|---|---|---|---|---|---|---|---|
| | 38 | 39 | 40 | 41 | 42 | 43 | 44 | 45 | 46 | 47 |
| Water | 5.2 | 5.3 | 6.1 | 6.7 | 6.2 | 6.2 | 6.3 | 5.9 | 6.5 | 6.0 |
| Tightly Held Water | 3.0 | 2.9 | 2.8 | 3.0 | 2.8 | 3.0 | 2.9 | 3.2 | 3.3 | 3.0 |
| % Extractable Material | 15.0 | 19.0 | 22.0 | 22.0 | 25.0 | 14.0 | 24.2 | 16.0 | 22.0 | 1.00 |
| ABSORPTION RATE | 8.5 | 3.0 | 2.0 | 16 | 2.5 | 7.0 | 5.0 | 7.5 | 6.5 | 30 |

The foams of Examples 41 and 47 were less hydrophilic than desired as can be seen by their high absorption rates. The foams of all the other Examples were satisfactory. The foams of Examples 43-46 were especially soft and uniform with distinct cosmetic odor.

EXAMPLES 48-57

These Examples illustrate the wide variety of combinations of isocyanate prepolymer, hydrophilic agent, adjuvant and wetting agent that may be used to form a hydrophilic foam composition in accordance with the present invention. The composition of the reactant compositions used are set forth in Table XIII.

The retained liquid, tightly held liquid, extractable materials and absorption rate for the foam compositions of these Examples are set forth in Table XIV.

TABLE XIII

| REACTANT COMPOSITION | EXAMPLE No. | | | | | | | | | |
|---|---|---|---|---|---|---|---|---|---|---|
| | 48 | 49 | 50 | 51 | 52 | 53 | 54 | 55 | 56 | 57 |
| I. PREPOLYMER | | | | | | | | | | |
| Prepolymer A | 20.00 | 20.00 | 10.00 | 10.00 | 20.00 | 15.00 | 10.00 | 10.00 | 10.00 | 10.00 |
| Prepolymer B | | | 10.00 | 10.00 | | 5.00 | 10.00 | 10.00 | 10.00 | 10.00 |
| II. HYDROPHILIC AGENT | | | | | | | | | | |
| A | 2.00 | 2.00 | 2.00 | 2.00 | 4.00 | 2.00 | 2.00 | 2.00 | 2.00 | 2.00 |
| D | | 1.00 | 1.00 | 1.00 | 2.00 | 2.00 | 2.00 | 2.00 | 2.00 | 2.00 |
| III. WATER | | | | | | | | | | |
| Normal saline (0.85% NaCl) | 14.50 | 14.50 | 14.50 | 14.50 | 14.50 | 14.50 | 12.00 | 23.00 | 14.50 | 14.50 |

TABLE XIII-continued

| REACTANT COMPOSITION | EXAMPLE No. | | | | | | | | | |
|---|---|---|---|---|---|---|---|---|---|---|
| | 48 | 49 | 50 | 51 | 52 | 53 | 54 | 55 | 56 | 57 |
| IV. ADJUVANT SYSTEM | | | | | | | | | | |
| glycerin | 5.00 | 5.00 | 5.00 | 15.00 | 10.00 | 9.00 | 13.00 | 10.00 | 10.00 | 10.00 |
| Honey | 1.00 | 1.00 | 3.00 | 1.00 | 1.00 | 1.00 | 0.50 | 0.50 | 0.15 | |
| propylene glycol | | 1.00 | 2.00 | | | | | | | |
| V. WETTING AGENT | | | | | | | | | | |
| Pluronic F-68 | 2.50 | 2.50 | 2.50 | 2.50 | 2.50 | 2.50 | 2.00 | 4.00 | 2.50 | 2.50 |
| Pluronic L-62 | | | | | | | | 1.00 | | |
| Crodesta SL-40 | | 1.00 | | | | | | | | |
| VI. OTHER | | | | | | | | | | |
| FD & C Blue No. 1 Solution | 0.05 | 0.05 | 0.05 | 0.05 | 0.05 | 0.05 | 0.05 | 0.05 | 0.05 | 0.05 |

TABLE XIV

| RETAINED LIQUID | EXAMPLE NO. | | | | | | | | | |
|---|---|---|---|---|---|---|---|---|---|---|
| | 48 | 49 | 50 | 51 | 52 | 53 | 54 | 55 | 56 | 57 |
| Water | 5.1 | 6.5 | 6.3 | 6.9 | — | 11.1 | 12.2 | 8.5 | 11.6 | 12.2 |
| Tightly Held Water | 2.6 | 4.1 | 4.6 | 5.0 | — | 6.3 | 6.7 | 6.0 | 8.1 | 6.3 |
| % Extractable Material | 25.0 | 17.0 | 24.0 | 29.3 | — | 29.0 | 26.3 | 30.0 | 26.8 | 28.0 |
| ABSORPTION RATE | 2.0 | 1.5 | 2.0 | 2.0 | 1.0 | 1.5 | 2.0 | 9.0 | 1.0 | 1.0 |

The foams of Examples 48, 50, 56 and 57 were acceptable. The foams of Examples 51 through 54 were more porous than desired, although the liquid retention and extractability were good. The amount of extractable material for the foam of Example 49 was somewhat low.

We claim:

1. A composite for use in a wound dressing comprising a substrate, a medically acceptable adhesive deposited on said substrate and a hydrophilic foam composition carried by said adhesive, said composition comprising the in situ reaction product of:
   (a) an isocyanate-capped polyether prepolymer,
   (b) a polymeric hydrophilic agent capable of absorbing water,
   (c) an adjuvant comprising an alcohol selected from the group consisting of water soluble monols, diols and polyhydric alcohols,
   (d) a wetting agent, and
   (e) water, said hydrophilic foam composition releasably carrying said adjuvant so that said foam composition is capable of absorbing an external liquid and tightly carrying said liquid in preference to at least a portion of said adjuvant so that said adjuvant is released in the presence of the external liquid.

2. A composite for use in a wound dressing comprising a substrate, a medically acceptable adhesive deposited on said substrate and a hydrophilic foam composition, said composition comprising the in situ reaction product of:
   (a) an isocyanate-capped polyether prepolymer, wherein said prepolymer is a member selected from the group consisting of isocyanate-capped polyether polyols having an isocyanate equivalent weight of from about 0.5 meg/g to about 3.0 meg/g,
   (b) a hydrophilic agent capable of absorbing water, said hydrophilic agent being a member selected from the group consisting of starch grafted copolymers of acrylate salts, starch grafted copolymers of acrylamide salts, polyacrylate salts and mixtures thereof;
   (c) an adjuvant comprising an alcohol, said adjuvant being a member selected from the group consisting of ethanol, isopropyl alcohol, propylene glycol, polyethylene glycol, polypropylene glycol, glycerine, 1,2,4-butanetriol, trimethylolpropane, sorbitol, pentaerythritol, and mixtures thereof; said reactant composition including;
   (d) a wetting agent selected from the group consisting of block copolymers of ethylene oxide and propylene oxide, ethoxylated sorbitan fatty acid esters, glycerol esters, polyglycerol esters, silicone fluids and mixtures thereof, and
   (e) water, said water being a member selected from the group consisting of deionized water, distilled water and normal saline.

3. A method for making a composite for use in a wound dressing comprising:
   providing a substrate,
   applying a medically acceptable adhesive to said substrate,
   applying a reactant composition to said adhesive, said reactant composition comprising an isocyanate-capped polyether prepolymer, a polymeric hydrophilic agent capable of absorbing water, an adjuvant comprising an alcohol selected from the group consisting of water soluble monols, diols and polyhydric alcohols, a wetting agent and water, and
   curing said reactant composition while it is in contact with said adhesive.

4. A method for making a composite for use in a wound dressing comprising:
   providing a substrate,
   applying a medically acceptable adhesive to said substrate,
   applying a reactant composition to said adhesive, said reactant composition comprising
   (a) an isocyanate-capped polyether prepolymer having an isocyanate equivalent weight of from about 0.5 meq/g to about 3 meq/g;
   (b) a hydrophilic agent capable of absorbing water and having a fluid uptake of at least about 50 ml of water per gram of said agent, and wherein said hydrophilic agent comprises a hydrophilic material which is a member selected from the group consisting of starch grafted copolymers of acrylate salts, starch grafted copolymers of acrylamide salts, polyacrylate salts and mixtures thereof;

(c) an adjuvant comprising an alcohol selected from the group consisting of ethanol, isopropyl alcohol, propylene glycol, polyethylene glycol, polypropylene glycol, glycerin, 1,2,4-butanetriol, trimethylolpropane, pentaerythritol sorbitol, and mixtures thereof;

(d) a wetting agent comprising a non-ionic surfactant selected from the group consisting of block copolymers of ethylene oxide and propylene oxide, ethoxylated sorbitan fatty acid esters, glycerol esters, polyglycerol esters, silicone fluids and mixtures thereof; and (e) water, curing said reactant composition while it is in contact with said adhesive to form a foam composition that is unreleasably attached to said adhesive, said foam composition releasably carrying said adjuvant so that said foam composition is capable of absorbing an external liquid and tightly carrying said liquid in preference to at least a portion of said adjuvant so that said adjuvant is released from said foam composition in the presence of the external liquid.

5. A method for treating a wound comprising applying to the wound a composite as claimed in claim 1.

6. A method for treating a wound comprising applying to the wound a composite as claimed in claim 2.

7. A composite made by the method of claim 3.

8. A composite made by the method of claim 4.

9. A method for treating a wound comprising applying to the wound a composite as claimed in claim 7.

10. A method for treating a wound comprising applying to the wound a composite as claimed in claim 8.

* * * * *